(12) United States Patent
Leard

(10) Patent No.: US 8,480,246 B2
(45) Date of Patent: Jul. 9, 2013

(54) SYSTEM AND METHOD FOR REDUCTION OF OPTICAL NOISE

(75) Inventor: Francis L. Leard, Sudbury, MA (US)

(73) Assignee: Rockwell Automation Technologies, Inc., Mayfield Heights, OH (US)

( * ) Notice: Subject to any disclaimer, the term of this patent is extended or adjusted under 35 U.S.C. 154(b) by 74 days.

(21) Appl. No.: 13/158,290

(22) Filed: Jun. 10, 2011

(65) Prior Publication Data

US 2012/0314410 A1 Dec. 13, 2012

(51) Int. Cl.
*F21V 9/16* (2006.01)

(52) U.S. Cl.
USPC ........ 362/84; 250/458.1; 250/362; 250/459.1

(58) Field of Classification Search
None
See application file for complete search history.

(56) References Cited

U.S. PATENT DOCUMENTS

| | | | |
|---|---|---|---|
| 2,247,969 A | | 7/1941 | Stewart |
| 4,655,586 A | * | 4/1987 | Stauffer ........................ 356/3.08 |
| 4,936,676 A | * | 6/1990 | Stauffer ........................ 356/623 |
| 5,485,530 A | | 1/1996 | Lakowicz et al. |
| 5,706,092 A | | 1/1998 | Stannard et al. |
| 6,784,603 B2 | | 8/2004 | Pelka et al. |
| 7,295,316 B2 | | 11/2007 | Boege et al. |
| 2004/0245444 A1 | | 12/2004 | MacDougall |
| 2007/0230175 A1 | | 10/2007 | Montgomery |
| 2009/0159691 A1 | | 6/2009 | Halbur et al. |
| 2009/0201577 A1 | * | 8/2009 | Laplante et al. .............. 359/355 |
| 2010/0177307 A1 | | 7/2010 | Rimke et al. |
| 2013/0015358 A1 | | 1/2013 | Leard |

OTHER PUBLICATIONS

Evident Technologies Forms Nightmarker Business Unit; The basis for a wavelength converter to be used in sensors: the ability to use much higher power IR sources and still be able to use silicon as a sensor; www.nightmarker.com/products/ir-paint; Oct. 7, 2008; 2 pages.
LED Backlighting / Nanosys; www.nanosysinc.com/what_we_do_led_backlighting/; May 23, 2011; 1 page.
U.S. Appl. No. 13/158,393; Notice of Allowance; United States Patent & Trademark Office; Oct. 17, 2012; 9 pages.

* cited by examiner

*Primary Examiner* — Britt D Hanley
(74) *Attorney, Agent, or Firm* — Whyte Hirschboeck Dudek S.C.; William R. Walbrun; John M. Miller

(57) ABSTRACT

A variety of methods and systems are described that relate to reducing optical noise. In at least one embodiment, the method includes, emitting a first light having a selected wavelength from a light source, receiving a reflected first light onto a phosphor-based layer positioned inside a receiver, the reflected first light being at least some of the emitted first light that has been reflected by an object positioned outside of a desired target location. The method further includes, shifting the wavelength of the received reflected first light due to an interaction between the received reflected first light and the phosphor-based layer, and passing the received reflected first light with respect to which the wavelength has been shifted through a light detector without detection.

23 Claims, 5 Drawing Sheets

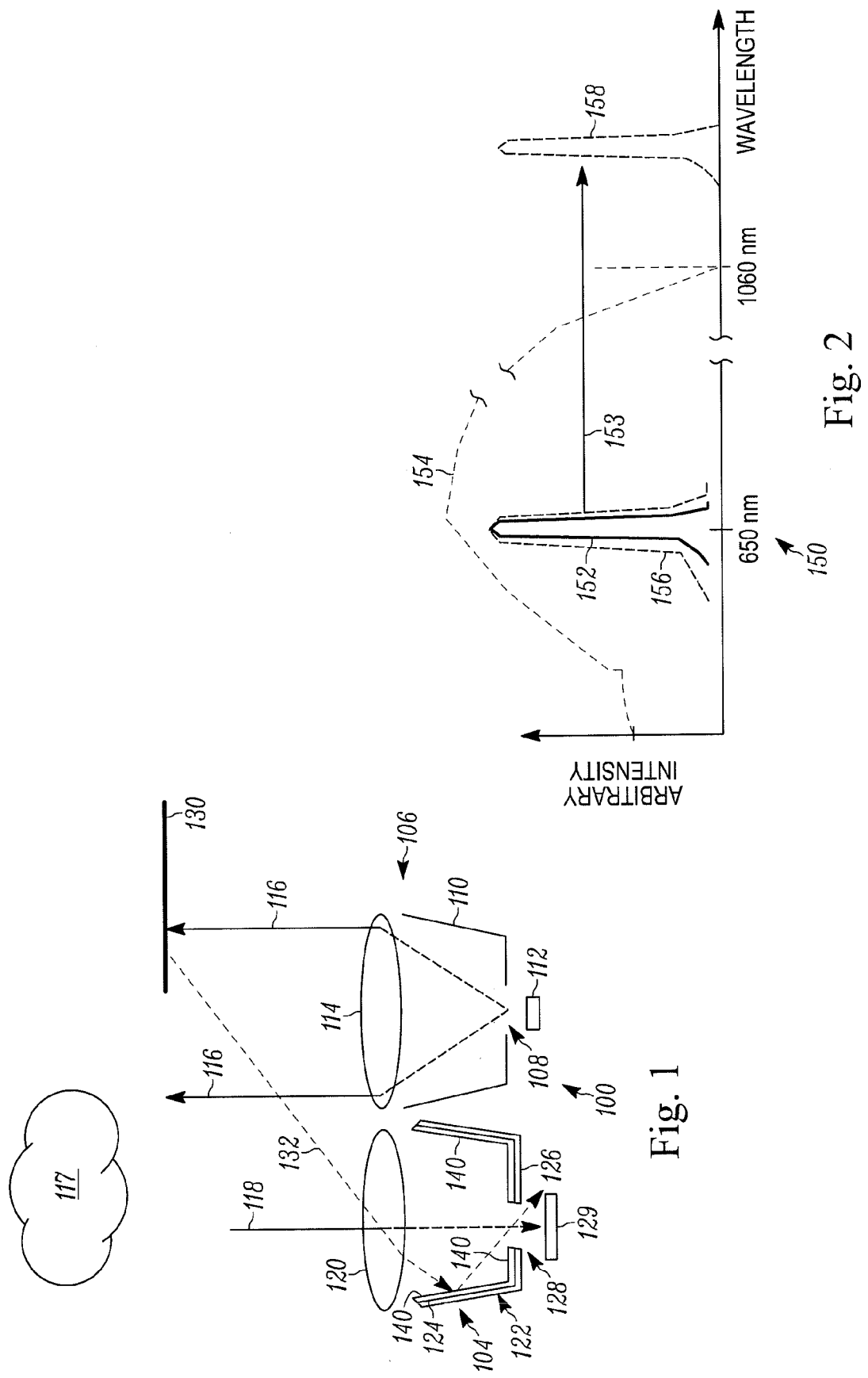

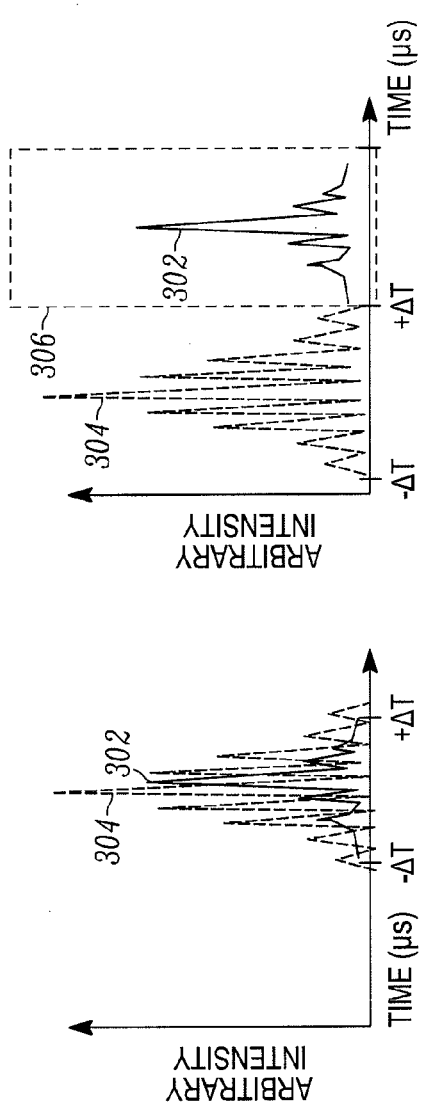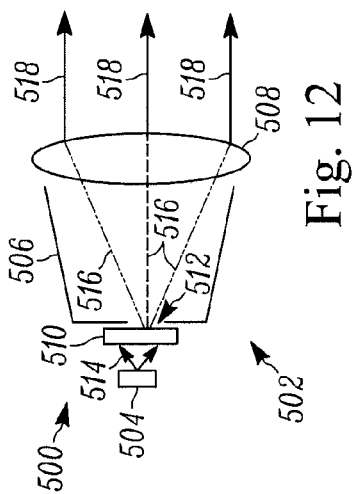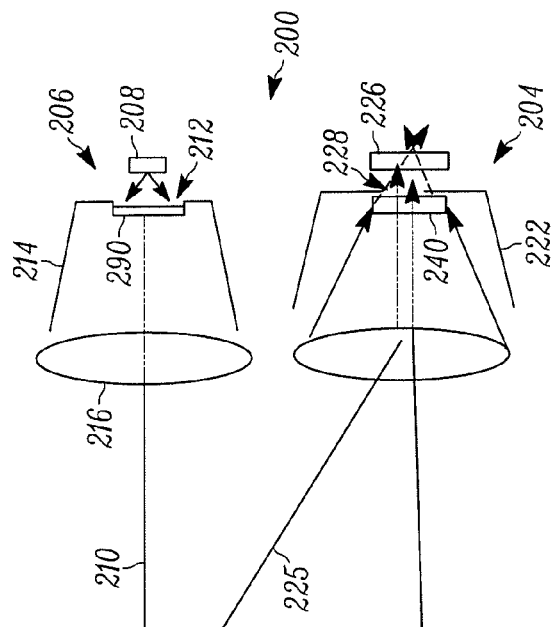

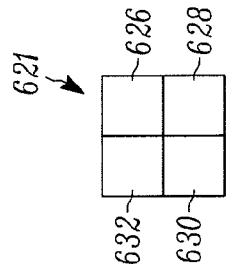
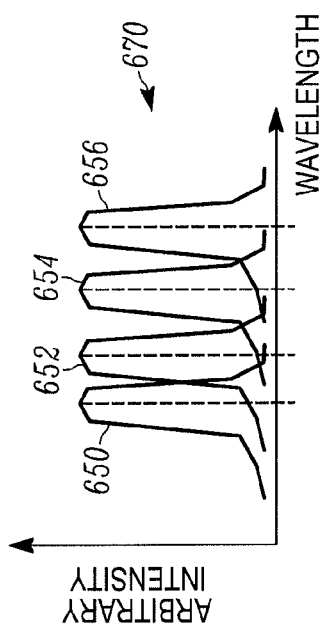
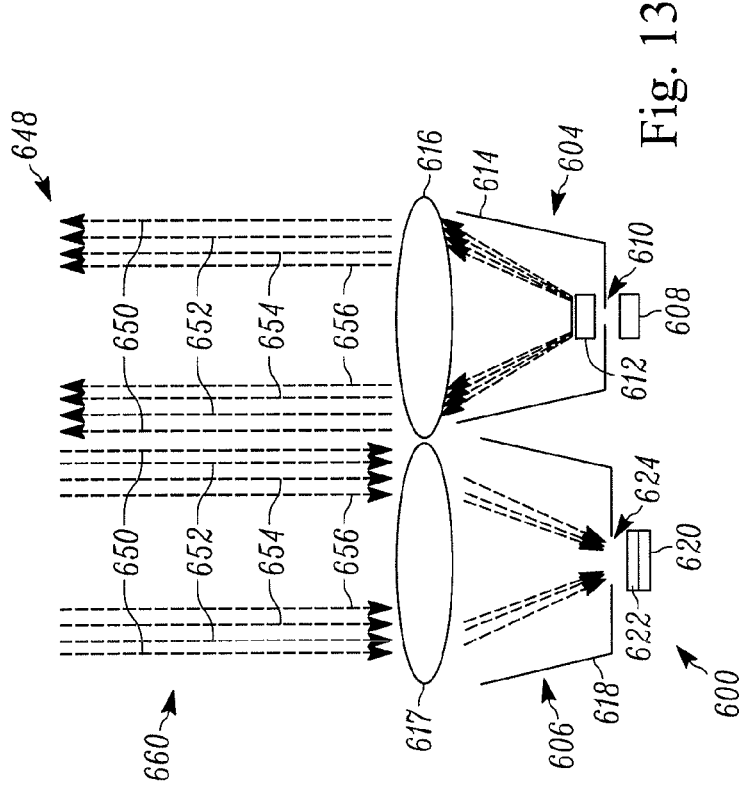
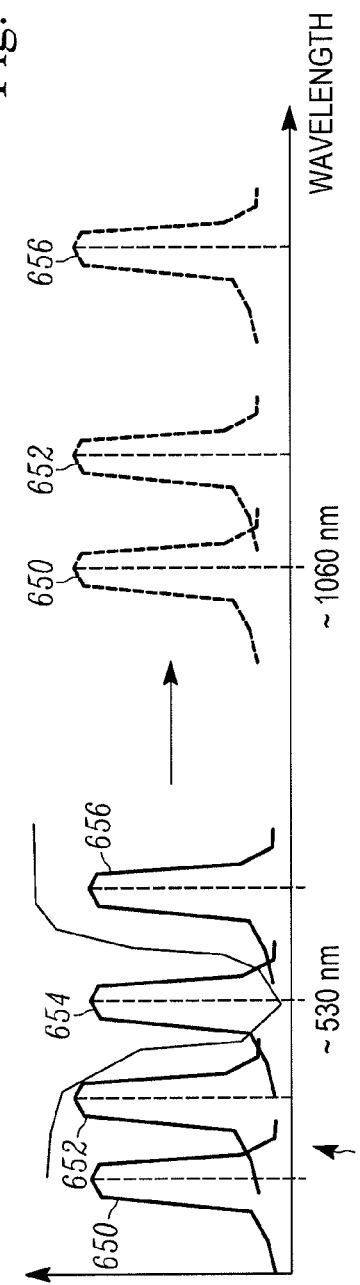

SYSTEM AND METHOD FOR REDUCTION OF OPTICAL NOISE

CROSS-REFERENCE TO RELATED APPLICATIONS

Not Applicable

STATEMENT REGARDING FEDERALLY SPONSORED RESEARCH OR DEVELOPMENT

Not Applicable

FIELD OF THE INVENTION

The present invention relates to the field of optical sensing systems and methods and, more particularly, to systems and methods for optical noise reduction as can be employed in relation to such optical sensing systems and methods.

BACKGROUND OF THE INVENTION

Optical or photoelectric sensors use light to sense targets without physical contact and are used in a wide variety of applications and environments, such as to sequentially detect the presence or absence of targets on a conveyor belt. Various types of optical sensors are available, such as light curtains, transmitted beam sensors, retro-reflective sensors, and diffuse sensors. Typically, each of these sensors includes a light source, such as a light emitting diode (LED) or a laser, and a photodetector for detecting light, such as a photodiode or phototransistor, and can also include one or more lenses to focus or narrow the beam of light emitted by the light source and/or to focus or narrow the received light for efficient detection by the photodetector. These sensors typically also include circuitry in communication with the photodetector for producing a voltage or current signal indicative of a characteristic of the sensed target, such as high and low voltage or current states for respectively indicating the presence and the absence of the target at a specified location.

The accurate sensing of targets can be rendered difficult under various conditions such as when the signal-to-noise ratio is very low. For example, some photoelectric sensors have limited ability to function reliably in the presence of various types of environmental noise, signals from other sensors, and/or interference from unintended targets, such as lambertian surfaces. In such circumstances, a given optical sensor can misconstrue one or more other signals (unintended signals, e.g., noise) as intended signals, and therefore generating a false detection within the sensor. In an effort to accommodate these issues, sensors are often detuned or otherwise modified to limit their capabilities in order to avoid detecting unwanted signals. Such modifications can often render the sensor substantially unsuitable for its intended use. For example, limiting the sensing range of a sensor to prevent sensing other adjacent signals can be too constricting for a particular process that requires longer range sensing. In other cases, to accommodate limited sources of noise, techniques involving modification of the transmitter and/or receiver channels have been attempted, but these techniques have proven to be expensive and have met with very limited success.

In addition, when one or more sensors are within another sensor's field of view, cross-talk can occur, rendering the sensors unreliable and requiring changes to the physical placement of various components in processes to attempt to accommodate the sensors' limitations. This can be a particular problem in manufacturing processes that often require numerous sensors to be located adjacent to each other on a single conveyor or across from each other on different conveyors.

Therefore, it would be advantageous if an improved system or method for use in relation to optical sensing systems and/or methods could be developed that would allow one or more of the drawbacks discussed above to be entirely or at least partly overcome.

BRIEF SUMMARY OF THE INVENTION

The present inventor has recognized the aforementioned disadvantages associated with conventional optical or photoelectric sensors and related sensing processes, and has further recognized that the implementation of a phosphor-based layer in relation to an optical/photoelectric sensor (for example, within a transmitter or receiver of such a sensor) can allow for enhanced sensor performance in which one or more of such disadvantages are entirely or at least partly overcome.

In at least some embodiments, a method for reducing optical noise includes, a first light having a selected wavelength from a light source, receiving a reflected first light onto a phosphor-based layer positioned inside a receiver, the reflected first light being at least some of the emitted first light that has been reflected by an object positioned outside of a desired target location. The method further includes shifting the wavelength of the received reflected first light due to an interaction between the received reflected first light and the phosphor-based layer, and passing the received reflected first light with respect to which the wavelength has been shifted through a light detector without detection. Further, in at least some embodiments, the phosphor-based layer includes at least one of a nano-phosphor and quantum dot phosphors.

In at least some other embodiments, a method for reducing optical noise includes, receiving a first light from a first light source, passing the first light through, or reflecting the first light at, a first phosphor-based layer, wherein due to the passing or reflecting at least one characteristic of at least one portion of the first light is modified. The method further includes receiving the at least one portion of the modified first light at a first light detector, wherein the at least one portion is received but not does not substantially influence an output of the first light detector. Further, in at least some embodiments, the method additionally includes emitting a second light from a second light source, the second light having a first wavelength, receiving the second light at the first fight detector subsequent to the second light being reflected by an object, and detecting the second light.

In at least yet some other embodiments, a method for reducing optical noise between devices includes, generating a first light from a first light source of a first transmitter, passing the first light through a first phosphor based layer shifting the wavelength of the first light to a first selected wavelength, and emitting the shifted first light from the first transmitter. The method further includes, generating a second light from a second light source of a second transmitter, passing the second light through a second phosphor based layer, shifting the wavelength of the second light to a second selected wavelength, different than the first wavelength, and emitting the shifted second light from the second transmitter. Additionally, the method includes, receiving the shifted second light at the first receiver, passing the second light through a third phosphor-based layer shifting the wavelength of the second light to a wavelength that exceeds or substantially exceeds the detection range of first receiver, and passing the second light through the first receiver without detection.

In at least yet further embodiments, a system for emitting light in a transmitter includes, a first transmitter having a first transmitter lens and a first optical housing with a first transmitter aperture, a first light source for emitting a first light, and a first phosphor-based layer positioned proximate to the first transmitter aperture and between the first light source and the first lens.

In at least yet still further embodiments, a system for reducing optical noise includes, a transmitter having a light source for emitting first light at a pre-selected wavelength, a receiver having an optical housing and a light detector, a receiver aperture positioned inside the receiver for receiving one or both of the first light and a second light and a phosphor-based layer situated inside the receiver for shifting the wavelength of one or both of the first and second light received into the receiver, to at least one wavelength value outside a wavelength detection range of the light detector.

In at least yet still even further embodiments, a system for reducing optical noise includes, a first transmitter having a first transmitter lens and a first optical housing with a first transmitter aperture, a first light source for emitting a multi-colored first light, and a first phosphor-based layer positioned proximate to the first transmitter aperture and between the first light source and the first lens. Additionally, the method can include a first receiver having a second phosphor-based layer and positioned to receive at least a portion of the multi-colored first light, and a first light detector positioned in the first receiver, having multiple colored pixels for sensing one or more of the colors in the multi-colored light.

Other embodiments, aspects, features, objectives, and advantages of the present invention will be understood and appreciated upon a full reading of the detailed description and the claims that follow.

BRIEF DESCRIPTION OF THE DRAWINGS

Embodiments of the invention are disclosed with reference to the accompanying drawings and are for illustrative purposes only. The invention is not limited in its application to the details of construction or the arrangements of components illustrated in the drawings. The invention is capable of other embodiments or of being practiced or carried out in various other ways. Like reference numerals are used to indicate like components. In the drawings:

FIG. 1 is a schematic view of an exemplary photoelectric sensor with a phosphor-based layer;

FIG. 2 is a graphical representation of exemplary light wavelength shifting experienced by the photoelectric system of FIG. 1;

FIG. 9 is a graphical representation of an exemplary sensor emission time signal and an exemplary HFFL's emission time signal;

FIG. 10 is a graphical representation of exemplary time dilation corresponding to the information provided in FIG. 9;

FIGS. 11 and 12 are additional schematic views of additional exemplary photoelectric sensors with phosphor-based layers;

FIG. 13 is a schematic view of another exemplary photoelectric sensor with a phosphor-based layer;

FIG. 14 is a graphical representation of exemplary light wavelengths associated with the photoelectric sensor of FIG. 13;

FIG. 15 is an exemplary multi-pixel array associated with the photoelectric sensor of FIG. 13; and FIG. 16 is a graphical representation of exemplary light wavelength shifting experienced by the photoelectric sensor of FIG. 13.

DETAILED DESCRIPTION OF THE PREFERRED EMBODIMENT

Figure 4:
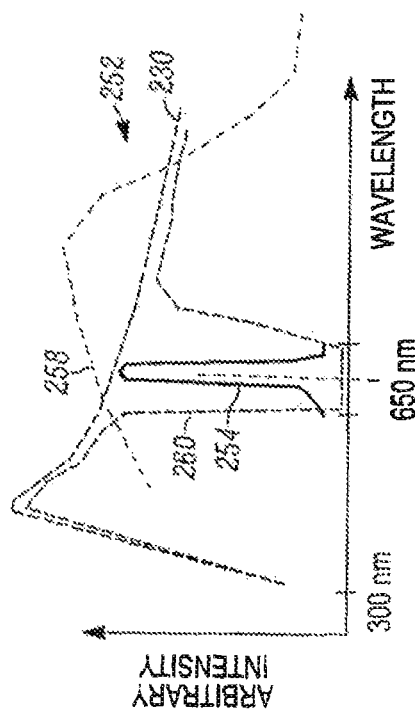
FIG. 4 is a graphical representation of exemplary light wavelengths associated with the photoelectric sensor of FIG. 3.

FIG. 1 shows in schematic form a cross-sectional side view of an exemplary optical or photoelectric sensor 100. It is to be understood that the sensor 100 as well as the other sensors discussed herein can include in some embodiments, one or more of numerous types of optical or photoelectric sensors including, for example, Through-Beam sensors (includes transmitter/receiver types, light curtain types) where the transmitter and receiver are in separate enclosures; Transceiver sensors (Reflective, Polarized Reflective, Diffuse, Background suppression types, Color sensors, Clear Object types, scanner types), Color Contrast sensors, and Time-Of-Flight sensors (through-beam types, transceiver types, and imaging types) where volumetric information is captured by the sensor opto-electronics circuits.

The sensor 100 shown in FIG. 1 particularly is depicted in operational relation to an exemplary target object 117 and a lambertian reflector 130. The sensor 100 includes a receiver 104 and a transmitter 106, wherein the receiver 104 and transmitter 106 are typically combined in a single housing (not shown), although other arrangements can be utilized, such as separate housings. The transmitter 106 includes a transmitter light source 112. The light sources discussed herein can include one or more of numerous light sources, such as a light emitting diode (LED), a laser, or any discrete wavelength or collection of discrete wavelength sources, etc. Further, in at least some embodiments, the light sources can include LEDs having specific light wavelength emissions, such as a blue LED. Additionally, although not to be understood as limiting, in some embodiments, the light sources can include any LED wavelength (or combination of wavelengths) from the ultraviolet spectrum (about 275 nm to about 450 nm), the visible spectrum (about 450 nm to about 750 nm), and the near infrared spectrum (about 750 nm to about 1050 nm).

In at least some embodiments, the transmitter light source 112 emits a light 116 through a transmitter aperture 108 of a transmitter optical housing 110. The emitted light 116 is passed through a transmitter lens 114, wherein the lens 114 can include one (or more) of a variety of lenses, such as a collimating lens, although other types of lenses can be used depending upon the embodiment. The emitted light 116 is projected away from the transmitter 106 and is intended to intercept a target object 117 that passes into the path of the emitted light 116. Emitted light 116 that strikes the target object 117 is reflected off the surface of the target object 117 and returns to the receiver 104 as intended reflected light 118. The intended reflected light 118 in turn is received at a receiver lens 120 that is positioned atop (or is otherwise associated with) a receiver optical housing 122. Similar to the transmitter lens 114, the receiver lens 120 can include a collimating lens or another type of lens.

In at least some embodiments, the receiver optical housing 122 includes an inner wall portion 124, a bottom portion 126, and a receiver aperture 128. Portion(s) of the intended reflected light 118 that enters the receiver optical housing 122 (via the receiver lens 120) can be reflected off the inner wall portion 124 and/or off the bottom portion 126, and some of this light can further then pass through the receiver aperture 128. Additionally, other portion(s) of the intended reflected light 118 can pass through the receiver aperture 128 without otherwise contacting the receiver optical housing 122. Those portion(s) of the intended reflected light 118 originating at the transmitter light source 112 that pass through the receiver aperture 128 are detected by a light detector 129, such as a photodiode positioned adjacent to the receiver aperture 128. In at least one embodiment, the light detector 129 can include a Time of flight (TOF) photodetector that utilizes multi-pixel imaging and/or single-pixel non-imaging arrays, such as a TOF photodetector as manufactured by Cedes, Ag. located in Landquart, Switzerland. It is to be understood that the term "light detector" used herein is intended to include one or more of various typical control circuit configurations (e.g., gating circuits) that process the output of a light detector and provide an indication of sensing light.

The position and angle of reflected light as it enters the receiver optical housing 122 is dependent on the position (and/or other characteristics, such as specific surface features) of an object off of which reflection occurs. With regard to an intended target object, such as the target object 117, when such object is in a pre-selected location relative to the receiver 104 and transmitter 106 (e.g., at the location of the target object 117 shown in FIG. 1), the intended reflected light 118 is generally or even exclusively directed through the receiver aperture 128 without contacting the inner wall portion 124 or the bottom portion 126. However, an unintended object other than the target object 117, such as a lambertian reflector 130, can also pass within range of the transmitter 106 and receiver 104 so as to be exposed to the emitted light 116. In such case, portion(s) of the emitted light 116 can be reflected off the unintended object (e.g., the lambertian reflector 130) to provide stray reflected light 132 as further shown in FIG. 1. Additionally, in at least some circumstances, an intended target object such as the target object 117 can also be responsible for portion(s) of stray reflected light such as the stray reflected light 132. For example, this can occur if portion(s) of the emitted light 116 reach and are reflected off the target object 117 before or after the target object 117 has moved to the pre-selected location. Although not shown, another source of stray light (not shown) can generate Regardless of the source of the stray reflected light 132, much of that stray reflected light is passed outside of the receiver lens 120. Nevertheless, commonly some of the stray reflected light 132 can and does enter the receiver optical housing 122. Most of the stray reflected light 132 is usually generated by an object (whether the target object 117 or another object such as the lambertian object 117) that is not situated in the pre-selected location. Therefore, the stray reflected light 132 usually enters the receiver optical housing 122 at an angle such that the stray reflected light 132 passed through the receiver lens 120 is directed to the inner wall portion 124 or the bottom portion 126 of the receiver optical housing 122. Upon arriving at the inner wall portion 124 and bottom portion 126, the stray reflected light 132 is then reflected off the inner wall portion 124 and/or the bottom portion 126 (and can continue to be reflected off of those portions on additional occasions), until it either exits the receiver optical housing 122 or is passed through the receiver aperture 128.

The light detector 129 in the receiver 104 includes a wavelength detection range, wherein the wavelength detection range is selected to include light having a specific wavelength that corresponds to the wavelength of the emitted light 116 sent out by the transmitter light source 112. That being the case, not only the intended reflected light 118 but also the stray reflected light 132 passing through the receiver aperture 128 typically is light that would be detectable by the light detector 129 to the extent it further passes through the receiver aperture 128, since both the intended reflected light and the stray reflected light 132 match the characteristics of the emitted light 116 from the transmitter light source 112 in terms of wavelength/frequency. However, to the extent portion(s) of the stray reflected light 132 did arrive at the light detector 129, this could result in a false detection signal being generated indicating the target object 117 as being in the pre-selected position even when it was not.

To prevent or substantially prevent such a false detection signal caused by the stray reflected light 132, in the embodiment of FIG. 1 the inner wall portion 124 and/or the bottom portion 126 of the receiver optical housing 122 is coated with a phosphor-based layer 140 that includes, for example, a nano-phosphor and/or quantum dot phosphor mixture. The phosphor-based layer 140 causes at least one characteristic of the stray reflected light 132 to be modified upon striking the phosphor-based layer coated on the inner wall portion 124 and/or the bottom portion 126.

More particularly, a nano-phosphor is composed of a few pure grains so that its efficiency is heightened by its manufacturing method and its component crystals can be tailored to emit at selected wavelengths or with selected relaxation times (time dilation function). The quantum dots are phosphors whose size and construction are tailored to allow both selected energizing wavelengths and selected emission wavelengths. When the phosphor-based layer 140 includes a nano-phosphor mixture, it can be tailored to accept certain wavelengths that would be somewhat independent of its chemical make-up and capable of shifting these wavelengths efficiently to a longer wavelength, dependent on the construction of the nano-phosphors. In addition, when the phosphor-based layer 140 includes a quantum dot phosphor mixture, it can be tailored to accept certain wavelengths and to emit at tailored output wavelengths dependent on their size, chemistry, and composition, as discussed further below.

FIG. 2 depicts a graph of light wavelength relative to an arbitrary intensity. The intensity is designated arbitrary as it is dependent on desired pre-selected values inherent to the sensor. The intensity of emitted light from the transmitter is pre-selected, along with the intensity of light to be detected by the receiver, as such the values can be arbitrarily chosen to accommodate. In at least one embodiment, as seen in FIG. 2, the wavelength of the stray reflected light 132 is shifted to a different wavelength that exceeds the range of wavelengths that the light detector 129 is configured to detect. With this being the case, the wavelength-shifted stray reflected light 132 that manages to pass through the receiver aperture 128 subsequent to being reflected by one or more of the portions 124, 126 coated with the phosphor-based layer 140 will not be detected by the receiver 129. Rather, only the intended reflected light 118 (and possibly some portion of the stray reflected light 132) that passes through the receiver aperture 128 without contacting the phosphor-based coating 140 will be detected by the light receiver 129 and can trigger a signal that the target object 117 is in the pre-selected position.

More particularly with respect to FIG. 2, an exemplary light graph 150 shown indicates light wavelength along a horizontal axis and light intensity along a vertical axis as well as exemplary performance curves. As shown, in at least one exemplary embodiment the light source 112 can be configured to emit light, such as from an LED light source, having a wavelength of about 650 nm (nanometers), as illustrated by an emission curve 152. Also in one embodiment as shown, the light detector 129 is configured to detect light along a detection curve 154, which depending on the specific light detector 129 can include wavelengths of about 450 nm to about 1060 nm. In FIG. 2, the stray reflected light 132 further is illustrated as a false signal curve 156, which can be seen to overlap the emission curve 152 around 650 nm and therefore is included within the range detected by the receiver 104. As discussed above, the wavelength of the stray reflected light 132 can be shifted by the phosphor-based layer 140. In at least one embodiment as shown in FIG. 2, the wavelength of the stray reflected light 132 is shifted, as illustrated by an arrow 153, to a value that exceeds the receiver's detection capability, such as about 1060 nm. The false signal curve 156 is now positioned out of range of the receiver's detection (for clarity, that curve is now identified as a false signal curve 158), thereby preventing detection and a false detection signal.

In at least some embodiments, the phosphor-based layer 140 can include one or more nano-phosphors and/or quantum dot phosphors, which can be mixed together or layered. The phosphor-based layer 140 can include one or more layers that are applied onto a surface separately, or they can be mixed together and applied simultaneously.

As discussed above, optical/photoelectric sensors can generate false detection signals as a result of detecting stray reflected light generated by their own transmitter. In addition, optical/photoelectric sensors can also generate false detection signals as a result of detecting unintended light, such as stray light, from light sources other then the sensor itself (often considered "environmental noise"). One such example is a solar light source. A solar light source, such as the sun or the moon, includes a spectrum of light that is detectable by a typical light detector and therefore can generate noise that reduces the reliability of a photoelectric sensor.

Figure 3:
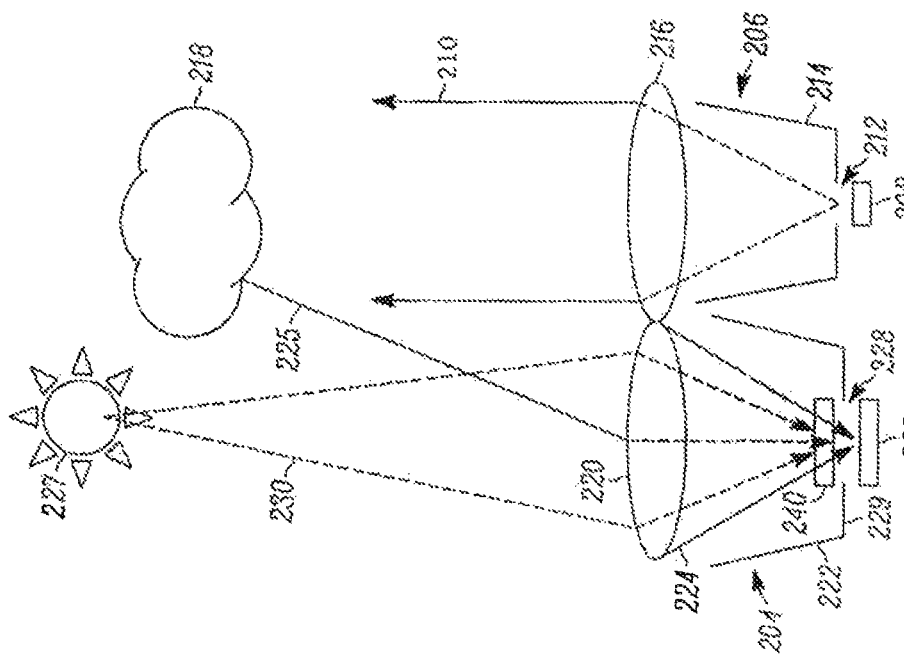
FIG. 3 is a schematic view of another exemplary photoelectric sensor with a phosphor-based layer.

Further, in this regard, referring to FIG. 3, a schematic cross-sectional side view of an exemplary photoelectric sensor 200 is shown in operational relation to an exemplary target object 218 and a solar light source 227. The photoelectric sensor 200 includes a receiver 204 and a transmitter 206. Similar to the photoelectric sensor 100, the transmitter 206 includes a transmitter light source 208 for emitting light through an aperture 212 of a transmitter optical housing 214. The emitted light is passed through a transmitter lens 216, where in at least one embodiment the transmitter lens 216 is a collimating lens, which can directionally emit light from the transmitter 206. The emitted light is directed towards a pre-selected location for the target object 218 to be detected.

Further as shown, the receiver 204 includes a receiver lens 220 positioned atop a receiver optical housing 222. Similar to the transmitter lens 216, the receiver lens 220 can, in at least one embodiment, include a collimating lens that can be used to direct incoming light into a field of view 224 of a light detector 226. The field of view 224 of the light detector 226 is determined by the size and shape of a receiver aperture 228 positioned along an optical housing bottom portion 229. In at least one embodiment, the field of view 224 extends conically downward from the receiver lens 220, through the receiver aperture 228, to the light detector 226. Similar to the light detector 129 discussed above, the light detector 226, as well as other embodiments of light detectors discussed herein, includes a wavelength detection range, wherein the wavelength detection range is selected to include light having a specific wavelength.

As seen in FIG. 3, light emitted from the transmitter 206, identified as emitted light 210, is intended to allow for detection of when the target object 218 is at a pre-selected locations (such as the location of that object illustrated in FIG. 3). More particularly, the emitted light 210 is reflected off the target object 218 and received as intended reflected light 225 by the receiver 204 for detection by the light detector 226. Detection of the intended reflected light 225 generates a valid detection signal. A false detection signal can occur when other light sources, such as the sun 227, emit solar light 230 (e.g., sunlight), that can be directed into the field of view 224 of the receiver 204, particularly if the solar light 230 includes a spectrum of light that encompasses a broad range of wavelengths (e.g., from 300 nm to greater than 1500 nm) some or all of which are in the range of detection of the light detector 226.

To limit the occurrence of false detection signals by other light sources, such as the solar light 230, in the present embodiment a phosphor-based layer 240 that includes, for example, a nano-phosphor and/or quantum dot phosphor mixture, can be provided to filter the received light (including both the intended reflected light 225 and the solar light 230) prior to receipt by the light detector 226. The phosphor-based layer 240 in this embodiment is positioned inside the optical housing 222 over the receiver aperture 228, between that aperture and the receiver lens 220. When the solar light 230 passes through the phosphor-based layer 240, at least one characteristic of the solar light 230 (but not the intended reflected light 225) can be modified, such as a shift in wavelength. For reasons discussed below, the occurrence of false detection signals is eliminated or reduced thanks to the modification caused by the phosphor-based layer 240.

Referring to FIG. 4, an exemplary light graph 252 is shown that includes a horizontal axis corresponding to light wavelength and a vertical axis corresponding to arbitrary light intensity. Further as shown on the light graph 252, the emitted light 210 from the transmitter 206 is illustrated by an emission curve 254 to be within a specific wavelength band, such as a wavelength of about 650 nm (nanometers), as found in typical LED light sources. The solar light 230 by contrast has a larger wavelength band that encompasses the wavelengths of the emission curve 254. Additionally, the light graph 252 includes a detection curve 258 representing the detection range of the light detector 226. As shown, both the emitted light 210 corresponding to the emission curve 254 and portion(s) of the solar light 230 are at wavelengths encompassed within the detection curve 258 that are detectable by the light detector 226.

Figure 5:
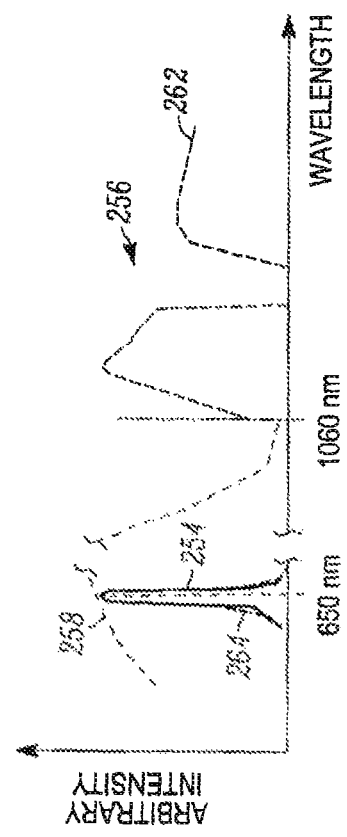
FIG. 5 is a graphical representation of exemplary light wavelength shifting experienced by the photoelectric sensor of FIG. 3.

Referring additionally to FIG. 5, as discussed above, to limit the amount of solar light 230 passed to the light detector 226, the phosphor-based layer 240 shifts the solar light 230 to a wavelength value outside the range of the wavelength that the light detector 226 is configured to detect. More particularly, the phosphor-based layer 240 shifts the wavelengths of at least some portion of the solar light 230 to wavelengths outside of the wavelength limits of the detection curve 258, for example to wavelengths above 1060 nm. As the solar light 230 includes some light portion(s) of wavelengths in the range of the intended reflected light 225 (about 650 nm in this example), those portion(s) of the solar light 230 would not be shifted/filtered out.

The phosphor-based layer 240 includes, in this example, a composition of materials that targets the solar light 230 situated outside the wavelength (or wavelength range) of the intended reflected light 225, as shown by a layer curve 260 in FIGS. 4 and 5. Wavelengths of solar light 230 that fall within the layer curve 260 are substantially shifted out of the detection curve 258, as illustrated in FIG. 5 as shifted light 262. The remaining solar light 230 situated in the same wavelength band as the intended reflected light 225 remains, although the intensity of the integrated power level (illustrated in FIG. 5 as a power level curve 264) of the remaining solar light 230 has been at least partially reduced. More particularly, the intensity of the integrated power level is diminished to a level below the intensity of the emission curve 254 for the intended reflected light 225.

In the present embodiment, it is particularly the reduction in the intensity of the integrated power level that allows for false detection signals to be eliminated/reduced. The sensor 200 in the present embodiment includes a receiver circuit (not shown) in communication with the light detector 226, where the receiver circuit is configured to detect light only within a specific intensity level at a particular wavelength. Given the operation of this receiver circuit, and given the reduction in intensity level of the solar light 230, the solar light no longer generates false detection signals, thereby allowing the sensor 200 to be used in locations where solar light is present.

Figure 6:
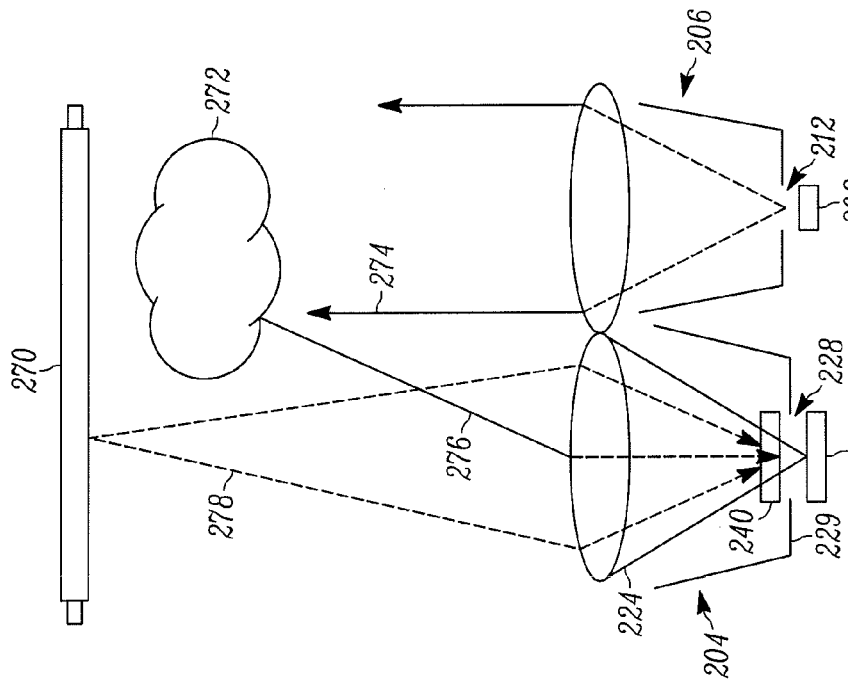
FIG. 6 is a schematic view of another exemplary photoelectric sensor with a phosphor-based layer.

Similar to the aforementioned application with a solar light source, the phosphor-based layer 240 can also be utilized to reduce noise associated with other light sources, such as a high frequency fluorescent light (HFFL) source. FIG. 6 illustrates the sensor 200 with reference to an HFFL light source 270 and a target object 272. The transmitter light source 208 provides emitted light 274 (again via the lens 216) for reflection off the target object 272. As discussed above, the transmitter light source 208 can include, for example, an LED that emits light at a wavelength of about 650 nm. When the target object 272 is in a pre-selected location, the emitted light 274 is reflected off the target object 272 as intended reflected light 276 and directed (again via the lens 220 and the phosphor-based layer 240) through the receiver aperture 228 for detection by the light detector 226.

Figure 7:
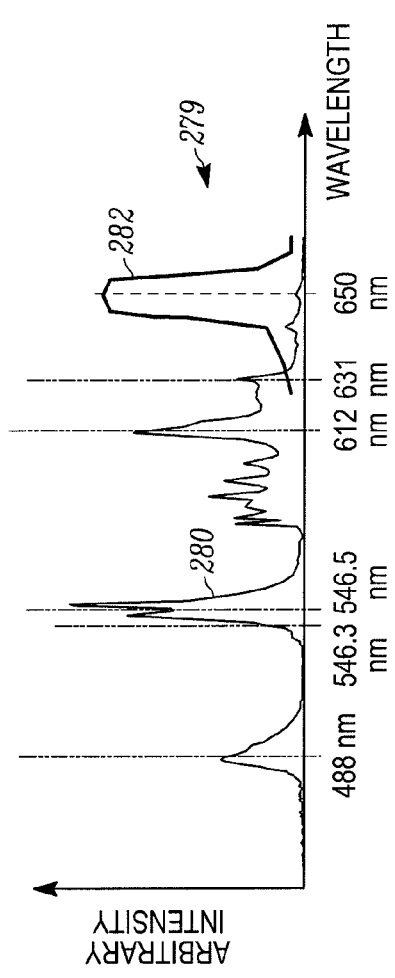
FIG. 7 is a graphical representation of exemplary light wavelengths associated with the photoelectric sensor of FIG. 6.

Referring to FIG. 7, an exemplary light graph 279 is shown that again (like FIG. 4) includes a light wavelength horizontal axis and light intensity vertical axis. Sensors in environments that include HFFL light source such as the light source 270 are subjected to HFFL light such as the light 278 that can particularly include an HFFL wavelength band (shown as a HFFL signal curve 280) that extends from about 300 nm to about 900 nm, including numerous intensity peak points, such as 488 nm, 546.3 nm, 546.5 nm, 612 nm, and 631 nm. Although the peaks of the HFFL light 278 are positioned at wavelengths apart from the wavelengths of the emitted light 274 from the transmitter light source 208 as represented by an emission curve 282, the HFFL light can nevertheless create substantial noise adjacent to the emission curve 282 (which in the present embodiment is situated at about 650 nm).

In the present embodiment one method for reducing the effect of noise generated by the HFFL light source 270 is to utilize the phosphor-based layer 240 to shift the wavelengths of the HFFL light 278 to a wavelengths outside of the sensitivity of the light detector 226, prior to receipt by the light detector 226. Similar to its use with other light sources, the phosphor-based layer 240 includes one or more materials with a composition that targets the wavelengths of the light sources to be addressed. The HFFL light 278 directed towards the receiver aperture 228 is passed through the phosphor-based layer 240 prior to the receipt by the light detector 226.

Figure 8:
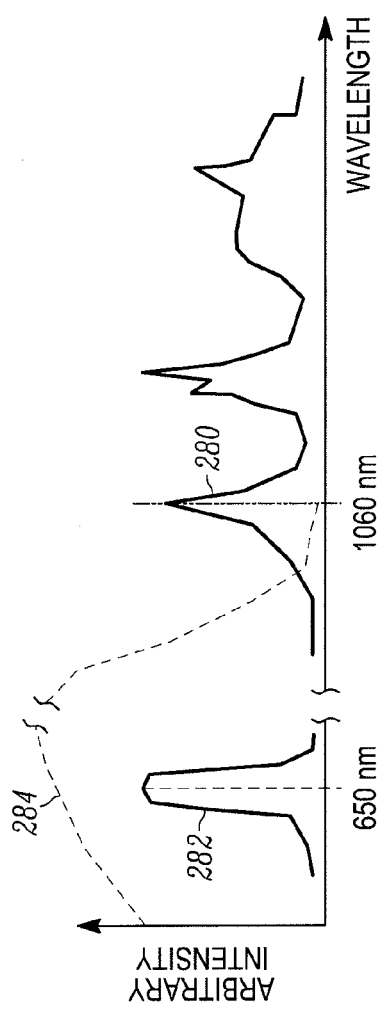
FIG. 8 is a graphical representation of exemplary light wavelength shifting experienced by the photoelectric sensor of FIG. 6.

As seen in FIG. 8, the phosphor-based layer 240 shifts the wavelength of the HFFL light 278 such that the HFFL signal curve 280 is shifted to at least partially extend beyond the detection curve 284. Positioning the HFFL signal curve 280 at least partially beyond, if not substantially or completely beyond the detection curve 284, eliminates the effects of at least some of the noise generated by the HFFL light source 270.

Another method for reducing the effect of noise generated by a light source, such as the HFFL light source 270, is to utilize the phosphor-based layer 240 to time dilate the HFFL's emission time signal of the HFFL light 278. To accomplish the time dilation, the phosphor-based layer 240 can include nano-phosphors and/or quantum dot phosphors that serve to down-shift the HFFL's emission time signal to values outside of a gating circuit band in the receiver 204. The phosphor-based layer 240 can include one or more layers, such that wavelength shifting, as discussed above, and/or time dilation can be performed.

Referring to FIGS. 9 and 10, various exemplary time waveforms are graphically depicted relative to horizontal axes in units of time and vertical axes in units of arbitrary intensity. FIG. 9 shows a graphical representation of an exemplary sensor emission time signal 302 and an exemplary HFFL's emission time signal 304. The exemplary sensor emission time signal 302, which belongs to either the emitted light 274 or the intended reflected light 276, is received at the phosphor-based layer 240. In addition, the HFFL's emission time signal 304, which belongs to the HFFL light 278, is also received at the phosphor-based layer 240. As seen in FIG. 9, as the HFFL light source 270 operates at the same temporal signal and similar wavelength as the sensor 200, the HFFL's emission time signal 304 overpowers the sensor emission time signal 302. Therefore, without modification by the phosphor-based layer 240 inside the receiver 204, the HFFL light 278 can generate enough noise to trigger a false detection signal.

FIG. 10 depicts the signals 302, 304 as they are received at the light detector 226 of the transmitter 206 after they have passed through the phosphor-based layer 240. As seen in FIG. 10, the sensor emission time signal 302 retains the same frequency response, while the frequency response of the HFFL's emission time signal 304 is time dilated away from the sensor emission time signal 302 along the time axis. Also as seen in FIG. 10, the sensor emission time signal 302 maintains its position, which is inside a gating circuit frequency response band 306, while the time dilated HFFL's emission time signal 304 is now positioned outside the gating circuit frequency response band 306.

The gating circuit frequency response band 306 is a predetermined function of a gating circuit (not shown) of the sensor 200. The gating circuit is used to pass photocurrent that is within the frequency response band 306 from the light detector 226 to an amplifier (not shown) in the sensor 200. The amplifier can then be used to trigger a detection signal. As the time dilated HFFL's emission time signal 304 is now positioned outside the gating circuit frequency response band 306, the photocurrent that is generated by the light detector 226 in response to the time dilated HFFL's emission time signal 304 is modulated at a different time band. Therefore, this photocurrent would not be allowed to pass through the gating circuit to the amplifier, while photocurrent from the sensor emission time signal 302 would be passed through the gating circuit. In this manner, the noise from the HFFL light 278 is negated or substantially negated, while the light received from the transmitter 206 remains unaffected.

Although the use of time dilation has been discussed with reference to HFFL light sources, both time dilation and wavelength shifting using the phosphor-based layer 240 can be utilized to improve sensor response by the reduction or elimination of environmental noise from one or more of other numerous sources of light. In addition, the aforementioned wavelength shifting can be used to prevent or substantially prevent cross-talk between different sensors, as discussed below.

When multiple photoelectric sensors are positioned within sight of each other cross-talk can occur. Cross-talk occurs when transmitted light from a first sensor is misinterpreted by a second sensor as light coming from its own transmitter. To avoid such cross-talk, each sensor can be configured to emit a particular and unique wavelength of light while its receiver would be configured to shift all wavelengths of light except for the unique wavelength emitted by its own transmitter. Therefore, each sensor would detect its own light, but would be blind to another sensor's transmitted light. Although traditional filters were substantially limited by their capability and cost, the vast number of available wavelengths of light that can be filtered using a phosphor-based layer allow for an extensive quantity of sensors to be situated within view of each other without suffering from cross-talk. In addition, the use of a phosphor-based layer in a transmitter and/or a receiver can be utilized to tailor a single sensor to a desired wavelength, even if cross-talk is not a primary concern. As a phosphor-based layer allows for the availability of numerous wavelengths of light to be pre-selected as a desired wavelength to communicate with, in at least some embodiments, one or more sensors can be configured to emit and/or detect wavelengths ranging from about 400 nm to about 1000 nm. In other embodiments, wavelengths exceeding 900 nm can be pre-selected as a desired wavelength for communication, while wavelengths below 900 nm can be effectively blocked by a phosphor-based layer. In still other embodiments, wavelengths not exceeding 600 nm can be pre-selected as a desired communication wavelength, with wavelengths exceeding 600 nm being effectively blocked by a phosphor-based layer.

Referring in particular to FIG. 11, the exemplary first sensor 200 is depicted positioned across from an exemplary second sensor 400. In at least some embodiments, the second sensor 400 can include similar components to the first sensor 200, such as a second receiver 404 and a second transmitter 406. The second receiver 404 can include a second receiver optical housing 407, a second light detector 408, and a second receiver lens 410. The second transmitter 406 can include a second light source 412, a second transmitter optical housing 414, and a second transmitter lens 416.

The first and second light sources 208, 412 can each be chosen by their inherent characteristics to have different narrow band wavelengths that can provide first and second emitted light 210, 418. In this manner, the first receiver 204 can utilize the first phosphor-based layer 240 in the receiver 204 to shift the wavelength of the light received from the second light source 412 so as not to be detected. Similarly, the second receiver 404 can utilize a second phosphor-based layer 420 to shift the wavelength of the light received from the first light source 208 to prevent detection by the second receiver 404. With each sensor filtering the emitted light from the other light source, cross-talk can be prevented or substantially prevented.

In at least some embodiments and as shown in FIG. 11, not only the layers 420 and 240 are present but also one or both of the transmitters 206, 406 can include one or more further phosphor-based layers 290, 422 placed between the light sources 208, 412 and their respective transmitter lens 216, 416, to shift the wavelength of light emitted by each to a desired wavelength. In at least some embodiments, the phosphor-based layer 290 is positioned over the first transmitter aperture 212, and the phosphor-based layer 422 is positioned over a second transmitter aperture 424. Using the phosphor-based layers 290, 422, the same types of light sources can used even if they have identical wavelengths of emitted light, as the light emitted from the transmitters 206, 406 will be affected by their respective phosphor-based layers 290, 422 to be different from each other. The first phosphor-based layer 240 would then further be selected to shift the wavelength of light that does not include the selected (shifted) wavelength of the first intended reflected light 225, and particularly does not include the wavelength of the second emitted light 418. Likewise, the second phosphor-based layer 420 would be selected to shift the wavelength of light that does not include the selected (shifted) wavelength of the second emitted light 210, and particularly does not include the wavelength of the first emitted light 210.

The aforementioned phosphor-based layers can include one or more layers that provide wavelength shifting and/or time dilation. In addition to limiting or preventing cross-talk, the phosphor-based layers can also reduce or eliminate environmental noise to significantly improve signal-to-noise ratio, as discussed above. Using these configurations, the reliability of various sensors can be substantially improved, such that many applications that previously precluded the use of such sensors are feasible. Additionally, although FIG. 11 illustrates only a pair of sensors, more than two sensors can be configured in the same way to emit a chosen wavelength of light and to allow only their respective transmitted light to be detected by their respective receivers.

In addition to enhanced sensing capabilities, the accurate transmission of light from a sensor can also be enhanced, as discussed with reference to FIG. 12, which depicts a transmitter 502 of an exemplary photoelectric sensor 500. In at least some embodiments, the transmitter 502 can include a light source 504, a transmitter optical housing 506, a transmitter lens 508, and a phosphor-based layer 510. In FIG. 12, the phosphor-based layer 510 is shown positioned between the transmitter aperture 512 and the light source 504, although the phosphor-based layer 510 can also be positioned between the transmitter aperture 512 and the transmitter lens 508. Positioning the light source 504 behind the phosphor-based layer 510 results in the source emitted light 514 from the light source 504 to be projected onto the phosphor-based layer 510. The phosphor-based layer 510 in turn becomes the new source of emitted light 516. In this configuration, the phosphor-based layer 510 can emit light uniformly across the aperture with no internal spatial structure. The emitted light 516 is then projected to the transmitter lens 508, which re-images the transmitter aperture 512 into the far field resulting in a uniform irradiance pattern of projected light 518.

The uniform irradiance pattern of projected light 518 serves to at least partially if not substantially eliminate hot/cold spots in the projection of the LED emission pattern due to electrical connections (wire-bonds and patterned electrodes). The hot/cold patterns limit the use of the sensor due to inability to control set-up of the sensor in the field to always hit a hot spot as opposed to a cold spot. Providing the uniform irradiance pattern of projected light 518 enhances a user's ability to integrate and operate a sensor. Similarly, positioning the phosphor-based layer 510 in from of the transmitter aperture 512 can also provide a uniform emission of light. Further, in at least some embodiments, as discussed above, the light source 504 can include LEDs having specific light wavelength emissions, such as a blue LED. Additionally, in at least some embodiments, the light source 504 can include an ultraviolet (UV) LED. In particular, a blue LED can provide an advantage over other colored LEDs, such as red, by providing more photons/current, resulting in a more efficient light source.

Traditionally, it has been difficult to provide accurate alignment between a sensor's light source, transmitter aperture, and transmitter lens, with the alignment of the transmitter aperture to transmitter lens being the most difficult to control. By utilizing the phosphor-based layer 510 and placing the light source 504 independent of the transmitter aperture 512, precise placement of the light source 504 is no longer critical, as the emitted light 514 from the light source 504 will be emitted uniformly from the transmitter aperture 512. In addition, the use of the phosphor-based layer 510 to pass a uniform light to the transmitter lens 508 allows for an emitted light 518 from the transmission lens 508 to be more accurately controlled.

Referring now to FIG. 13, another embodiment is shown that among other things, can be used to minimize cross-talk between sensors as well as provide color sensing capability. An exemplary sensor 600 includes a transmitter 604 and a receiver 606. The transmitter 604 includes a transmitter light source 608 for emitting light through a transmitter aperture 610 of a transmitter optical housing 614. Additionally, a phosphor-based layer 612 is provided between the transmitter aperture 610 and a transmitter lens 616, where in at least some embodiments, the phosphor-based layer 612 is positioned over the transmitter aperture 610.

Further as shown, the receiver 606 includes a receiver lens 617 positioned atop a receiver optical housing 618. The receiver lens 617 can, in at least one embodiment, include a collimating lens that can be used to direct incoming light into a light detector 620. In at least some embodiments, the light detector 620 includes a multi-pixel array. Additionally, a phosphor-based layer 622 is provided between the light detector 620 and the receiver aperture 624, where in at least some embodiments, the phosphor-based layer 622 is positioned over the light detector 620.

As seen in FIG. 13, emitted light 648 from the transmitter 604 includes a plurality of wavelengths associated with respective colors. This multiple wavelength light is provided by the light source 608 in conjunction with the phosphor-based layer 612. In at least some embodiments, the emitted light 648 can include purple 650, green 652, red 654, and black 656. As each color is different, they each have a unique wavelength value, as shown more particularly in FIG. 14 along an intensity/wavelength graph 670.

Referring again to FIG. 13, received light 660 is shown entering the receiver 606. This received light 660 can include emitted light 648, as well as emitted light from other transmitters disassociated with the sensor 600. At least a portion of the received light 660 enters the receiver aperture 624 and is then passed into the phosphor-based layer 622. As discussed above, the light detector 620 includes an exemplary multi-pixel array 621 (as shown in FIG. 15). Each colored pixel within the array can have a complementary phosphor-based mixture atop of it, as provided by the phosphor-based layer 622 positioned thereover. For example, a red pixel can include a phosphor-based layer 622 thereon that would shift the wavelength of all other colors, except red. In this manner, if red is included in the received light 660, the light detector 620 can provide such an indication to the sensor 600.

In an exemplary embodiment, the multi-pixel array 621 can include a purple pixel 626, a green pixel 628, a red pixel 630, and a black pixel 632. The phosphor-based layer 622 allows of each pixel to selectively shift the wavelengths of other colors in the received light 660. For example, as shown in the intensity/wavelength graph 671 in FIG. 16, if only red 654 is to be detected, the phosphor-based layer 622 over the red pixel 630 will shift the other colors outside of red 654, namely purple 650, green 652, and black 656 to a wavelength that exceeds or substantially exceeds the detection range of the light detector 620.

Further, this multi-pixel detection allows a small number of pixels to detect a much larger set of unique signals. More particularly, a phosphor-based layer in a single receiver can determine a much larger set of wavelength permutations transmitted by a transmitter, thereby performing the function of multiple receivers.

In another exemplary embodiment, color sensing can be performed by the sensor 600. To accomplish this, the sensor 600 includes a white light source 608 in the transmitter 604, but can omit the phosphor-based layer 612. In addition, the light detector 620 can include select pixel colors based on the color(s) being sensed. As the white light source 608 will emit all colors of light, when the emitted light 648 reflects off a target object (not shown), for which color sensing is desired, as received light 660, it will include various color signals and intensities that can be detected by the light detector 620 and interpreted by the sensor 600 using one or more algorithms to decipher the color of the target object.

As discussed above, the phosphor-based layer(s) can be situated in one or more of various positions relative to a light source, an aperture, and a lens, of one or both of a transmitter and a receiver. In addition, the phosphor-based layer can be integral with or coated onto a substrate, such as a plastic or glass carrier. One or more phosphor-based layers can be applied adjacent to or on top of other phosphor-based layers to provide multi-wavelength shifting properties and/or time dilation. Other methods of applying and positioning the phosphor-based layers can be utilized as well.

Numerous types of sensors and applications can benefit from the aforementioned phosphor-based layers. Applications such as photoelectric sensors used in manufacturing processes, light curtains, and safety scanners all can suffer from noise and cross-talk. In addition, security sensors, such as active and passive sensors, typically compete in an optically noisy environment and could increase their reliability immensely by shifting noise in wavelength or time. Further, any variation of imaging systems from UV to mid-range Infra-Red (IR) such as those found in cameras, scopes, night vision goggles, etc., can all benefit from wavelength shifting phosphor-based layers. One exemplary application can include using a UV imaging system, which incorporates one or more phosphor-based layers, to look into an oven for a specific wavelength in the presence of other wavelengths.

Various other types of applications can include optical devices/systems that rely on optical feedback (such as application in telecom, defense, meteorology, and ranging applications, master optical oscillators, and optical memory and computation). Notwithstanding the above examples, the present invention is intended to encompass numerous other embodiments and/or applications, and/or to satisfy a variety of other performance levels or criteria in addition to or instead of the above examples. It is specifically intended that the present invention not be limited to the embodiments and illustrations contained herein, but include modified forms of those embodiments including portions of the embodiments and combinations of elements of different embodiments as come within the scope of the following claims.

I claim:

1. A system for reducing optical noise comprising:
   a first transmitter having a first transmitter lens and a first optical housing with a first transmitter aperture;
   a first light source for emitting a first light;
   a first phosphor-based layer positioned proximate to the first transmitter aperture and between the first light source and the first lens, wherein the first phosphor-based layer wavelength shifts the first light passing through it to a first selected wavelength prior to emission from the first transmitter;
   a first receiver having a first light detector capable of detecting the first selected wavelength of the shifted first light; and
   a second phosphor-based layer positioned proximate to the first light detector for wavelength shifting at least a portion of incoming light that is not within the first selected wavelength to an additional wavelength that exceeds the detection range of the first light detector.

2. The system of claim 1,
   wherein the first light emitted from the light source is projected onto the first phosphor-based layer, thereby illuminating the first phosphor-based layer, and
   wherein the illumination of the first phosphor-based layer is uniformly projected from the first transmitter aperture to the first transmitter lens, resulting in a uniform irradiance pattern of light from the first transmitter lens.

3. The system of claim 2, wherein the light source includes at least one of a blue LED and an ultraviolet (UV) LED.

4. The system of claim 1 further including,
   a second transmitter having a second light source for emitting a second light;
   a third phosphor-based layer situated adjacent to the second light source for receiving the second light, wherein the third phosphor-based layer wavelength shifts of the second light passing through it to a second selected wavelength prior to emission from the second transmitter;
   a second receiver having a second light detector capable of detecting the second selected wavelength of the shifted second light; and
   a fourth phosphor-based layer positioned adjacent to the second light detector for wavelength shifting at least a portion of incoming light that is not within the second selected wavelength, to a further wavelength that exceeds the range of the second light detector.

5. The system of claim 1, wherein the first light from the first light source is a multi-colored light.

6. The system of claim 5, wherein the first light detector includes multiple pixels for sensing one or more of the colors in the multi-colored light.

7. The system of claim 6, wherein the first phosphor-based layer is positioned over each of the multiple pixels so that each respective one of the multiple pixels shifts respective light portions other than a respective light portion having a respective color associated with the respective one of the multiple pixels.

8. The system of claim 1, wherein the first phosphor-based layer includes at least one of a nano-phosphor and quantum dot phosphors.

9. The system of claim 1, wherein the first phosphor-based layer includes a mixture of two or more nano-phosphors or quantum dot phosphors.

10. The system of claim 1, wherein the first light source includes at least one of a blue LED and an ultraviolet (UV) LED.

11. A method for reducing optical noise comprising:
    generating a first light from a first light source of a first transmitter;
    passing the first light through a first phosphor based layer;
    wavelength shifting the first light to a first selected wavelength;
    emitting the shifted first light from the first transmitter;
    generating a second light from a second light source of a second transmitter;
    passing the second light through a second phosphor based layer;
    wavelength shifting the second light to a second selected wavelength, different than the first selected wavelength;
    emitting the shifted second light from the second transmitter;
    receiving the shifted second light at a first receiver;
    passing the shifted second light through a third phosphor-based layer;
    further wavelength shifting the shifted second light to an additional wavelength that exceeds or substantially exceeds the detection range of the first receiver; and
    passing the further shifted second light through the first receiver without detection.

12. The method of claim 11 further comprising:
    receiving at the first receiver the shifted first light reflected from a target object;
    passing the shifted first light through a fourth phosphor-based layer; and
    detecting at the first receiver, receipt of the reflected first light.

13. The method of claim 12, wherein the phosphor-based layer includes at least one of a nano-phosphor and quantum dot phosphors.

14. The method of claim 13, wherein the first light source includes at least one of a blue LED and an ultraviolet (UV) LED first light source.

15. A system for reducing optical noise comprising:
    a first transmitter having a first transmitter lens and a first optical housing with a first transmitter aperture;
    a first light source for emitting a multi-colored first light; and
    a first phosphor-based layer positioned proximate to the first transmitter aperture and between the first light source and the first lens; and
    a first receiver having a second phosphor-based layer and positioned to receive at least a portion of the multi-colored first light.

16. The system of claim 15, further including a first light detector positioned in the first receiver, having multiple colored pixels for sensing one or more of the colors in the multi-colored light.

17. The system of claim 16, wherein the second phosphor-based layer is positioned over each of the colored pixels and includes a unique composition at each colored pixel for wavelength shifting colored light that is different from the light of the colored pixel, prior to being received by the light detector.

18. The system of claim 17, wherein the second phosphor-based layer includes at least one of a nano-phosphor and quantum dot phosphors.

19. A method for reducing optical noise comprising:
    generating a first light from a first light source of a first transmitter;
    passing the first light through a first phosphor based layer;
    wavelength shifting the first light to a first selected wavelength;
    emitting the shifted first light from the first transmitter;

receiving the shifted first light and a second light at a first receiver;

passing the second light through a second phosphor-based layer;

wavelength shifting the second light to an additional wavelength that exceeds or substantially exceeds a detection range of the first receiver; and passing the second light through the first receiver without detection.

20. The method of claim 19 further comprising:

receiving at the first receiver the shifted first light reflected from a target object;

passing the reflected shifted first light through a third phosphor-based layer; and detecting, at the first receiver, receipt of the reflected shifted first light.

21. The method of claim 20, wherein either the third phosphor-based layer includes at least one of a nano-phosphor and quantum dot phosphors, or the first light source includes at least one of a blue LED and an ultraviolet (UV) LED first light source.

22. The method of claim 19, further comprising:

generating a third light from a second light source of a second transmitter;

passing the third light through a third phosphor based layer;

wavelength shifting the third light to a second selected wavelength, different than the first selected wavelength; and emitting the shifted third light from the second transmitter.

23. The method of claim 22, further comprising:

receiving the shifted third light at the first receiver; and passing the shifted third light through a fourth phosphor-based layer wherein, as a result of the passing of the shifted third light through the fourth phosphor-based layer, the shifted third light is not detected.

* * * * *